United States Patent
Guendel et al.

(10) Patent No.: US 11,996,197 B2
(45) Date of Patent: May 28, 2024

(54) GENERATING MODIFIED MEDICAL IMAGES AND DETECTING ABNORMAL STRUCTURES

(71) Applicant: Siemens Healthcare GmbH, Erlangen (DE)

(72) Inventors: Sebastian Guendel, Erlangen (DE); Arnaud Arindra Adiyoso, Nuremberg (DE); Sasa Grbic, Plainsboro, NJ (US); Dorin Comaniciu, Princeton Junction, NJ (US)

(73) Assignee: Siemens Healthineers AG, Forchheim (DE)

( * ) Notice: Subject to any disclaimer, the term of this patent is extended or adjusted under 35 U.S.C. 154(b) by 548 days.

(21) Appl. No.: 17/191,943

(22) Filed: Mar. 4, 2021

(65) Prior Publication Data
US 2021/0287799 A1    Sep. 16, 2021

Related U.S. Application Data

(60) Provisional application No. 62/988,429, filed on Mar. 12, 2020.

(30) Foreign Application Priority Data

Sep. 25, 2020    (DE) .................... 10 2020 212 113.3

(51) Int. Cl.
*G16H 50/00*    (2018.01)
*G06T 7/11*    (2017.01)
(Continued)

(52) U.S. Cl.
CPC .............. *G16H 50/20* (2018.01); *G06T 7/11* (2017.01); *G06T 7/337* (2017.01); *G16H 30/40* (2018.01);
(Continued)

(58) Field of Classification Search
CPC .......... G16H 50/20; G16H 30/40; G06T 7/11; G06T 7/337; G06T 2207/10081;
(Continued)

(56) References Cited

U.S. PATENT DOCUMENTS 10,691,980 B1 *    6/2020    Guendel ................... G06T 7/70
11,170,524 B1 *    11/2021    Mishra .................... G06T 5/005
(Continued)

FOREIGN PATENT DOCUMENTS

CN    110599593 A    * 12/2019    ............. G06T 17/00

OTHER PUBLICATIONS

Learning Face Image Super-Resolution through Facial Semantic Attribute Transformation and Self-Attentive Structure Enhancement (Mengyan Li; Zhaoyu Zhang; Jun Yu; Member, IEEE, and Chang Wen Chen, Fellow, IEEE; Mar. 2020) (Year: 2020).*
(Continued)

*Primary Examiner* — Khai M Nguyen
(74) *Attorney, Agent, or Firm* — Harness, Dickey & Pierce, P.L.C.

(57) ABSTRACT

A method is for generating modified medical images. An embodiment of the method includes receiving a first medical image displaying an abnormal structure within a patient, and applying a trained inpainting function to the first medical image to generate a modified first medical image, the trained inpainting function being trained to inpaint abnormal structures within a medical image. The method includes determining an abnormality patch based on the first medical image and the modified first medical image; receiving a second medical image of the same type as the first medical image; and including the abnormality patch into the second medical image to generate a modified second medical image. A method is for detecting abnormal structures using a trained detection function trained based on modified
(Continued)

second medical images. Systems, computer programs and computer-readable media related to those methods are also disclosed.

26 Claims, 8 Drawing Sheets

(51) Int. Cl.
  *G06T 7/33* (2017.01)
  *G16H 30/40* (2018.01)
  *G16H 50/20* (2018.01)

(52) U.S. Cl.
  CPC ............... *G06T 2207/10081* (2013.01); *G06T 2207/10088* (2013.01); *G06T 2207/10104* (2013.01); *G06T 2207/10108* (2013.01); *G06T 2207/10116* (2013.01); *G06T 2207/10132* (2013.01); *G06T 2207/20028* (2013.01); *G06T 2207/20081* (2013.01); *G06T 2207/20084* (2013.01); *G06T 2207/30064* (2013.01)

(58) Field of Classification Search
  CPC . G06T 2207/10088; G06T 2207/10104; G06T 2207/10108; G06T 2207/10116; G06T 2207/10132; G06T 2207/20028; G06T 2207/20081; G06T 2207/20084; G06T 2207/30064
  See application file for complete search history.

(56) References Cited

U.S. PATENT DOCUMENTS

| | | | | |
|---|---|---|---|---|
| 11,238,588 | B2* | 2/2022 | Kawagishi | G06N 5/04 |
| 2021/0104313 | A1* | 4/2021 | Mizobe | A61B 6/00 |
| 2021/0201042 | A1* | 7/2021 | Kim | G06N 3/045 |
| 2021/0334935 | A1* | 10/2021 | Grigoriev | G06T 3/0093 |
| 2022/0301118 | A1* | 9/2022 | Frey | G06T 11/60 |

OTHER PUBLICATIONS

Sogancioglu, E. et al.: "Chest x-ray inpainting with deep generative models" arXiv (2018), 1809.01471.
Huang et al:"Densely Connected Convolutional Networks" arXiv:1608. 06993, 2016.
Guan, Q. et al. "Diagnose like a Radiologist: Attention Guided Convolutional Neural Network for Thorax Disease Classification", 2018, arXiv:1801.09927v1; 2016.
Pathak, Deepak et al.: "Context Encoders: Feature Learning by Inpainting"; in: Conference: 2016 IEEE Conference on Computer Vision and Pattern Recognition; pp. 2536-2544: 2016; DOI: 10.1109/CVPR.2016.278.
X. Wang, Y. Peng, L. Lu, Z. Lu, M. Bagheri, and R. Summers, "Chestxray8: Hospital-scale chest x-ray database and benchmarks on weakly supervised classification and localization of common thorax diseases," in Proc. CVPR,2017, pp. 3462-3471.; 2017.
Yu et al., "Generative Image Inpainting with Contextual Attention", IEEE, Jan. 24, 2018, pp. 5505-5514; 2018.
Shiraishi et al: "Development of a Digital Image Database for Chest Radiographs With and Without a Lung Nodule: Receiver Operating Characteristic Analysis of Radiologists' Detection of Pulmonary Nodules", In:AJR. pp. 71-74, 2000.
Rajpurkar, Rranav et al. "CheXNet: Radiologist-Level Pneumonia Detection on Chest X-Rays with Deep Learning", 2017, arXiv:1711. 05225v1.
Li, Zhe et al. "Thoracic Disease Identification and Localization with Limited Supervision" 2018.
Yao L. et al:"Learning to Diagnose From Scratch by Exploiting Dependencies Among Labels", ArXiv (2018), 1710.10501.
Gundel, Sebastian et al. "Extracting and Leveraging Nodule Features with Lung Inpainting for Local Feature Augmentation" arXiv:2008. 02030v1 [eess.IV] Aug. 5, 2020 ( Accepted at MICCAI MLMI 2020).
Astaraki Mehdi: ; "Normal appearance autoencoder for lung cancer detection and segmentation."; In: Medical Image Computing and Computer Assisted Intervention-MICCAI 2019: 22nd International Conference, Shenzhen, China; Oct. 13-17, 2019; Proceedings, Part VI 22. Springer International Publishing; 2019; pp. 249-256.
Dvornik Nikita:; "Modeling visual context is key to augmenting object detection datasets." ; In: Proceedings of the European Conference on Computer Vision (ECCV); 2018; pp. 1-17.

* cited by examiner

GENERATING MODIFIED MEDICAL IMAGES AND DETECTING ABNORMAL STRUCTURES

PRIORITY STATEMENT

The present application hereby claims priority under 35 U.S.C. § 119(e) to U.S. provisional patent application No. 62/988,429 filed Mar. 12, 2020, the entire contents of which are hereby incorporated herein by reference.

FIELD

Example embodiments of the invention generally relate to image processing and in particular to medical imaging.

BACKGROUND

Lung cancer is one of the most frequent cancer worldwide. Combined with the high mortality rate, the efficiency of lung cancer diagnosis and treatment is of paramount importance. In 2019, over 228,000 new cases and over 140,000 estimated deaths are predicted in the US. The chance of surviving is higher when lung cancer is diagnosed in early cancer stages. The overall 5-year survival rate is approximately 70% for people with stage IA/B and 50% for people with stage IIA/B non-small lung cancer.

In the past years, automated systems have been established to support the radiologists in diagnosing abnormal structures (e.g., lung nodules) on chest X-ray images. Recent studies show that tremendous amount of nodule X-rays are required to compete with the nodule detection performance of radiologists. State-of-the art augmentation methods (e.g. known from the documents Q. Guan et al., "Diagnose like a radiologist: Attention guided convolutional neural network for thorax disease classification", arXiv 1801.09927 or P. Rajpurkarcan et al., "Chexnet: Radiologistlevel pneumonia detection on chest x-rays with deep learning", arXiv 1711.05225) can be used to increase the amount of training data. However, most of the augmentation methods hardly improve model performances as most techniques are applied on the whole image.

SUMMARY

At least one embodiment of the present invention provides and utilizes methods and systems for augmenting medical imaging training data, in order to improve the performance of resulting inference models. Embodiments of the present invention are directed to computer-implemented methods, systems, a computer-program product and a computer-readable storage medium. Advantageous embodiments and additional features are presented in the claims as well as in the following specification.

In the following, the solution according to at least one embodiment of the invention is described with respect to the systems as well as with respect to the methods. Features, advantages or alternative embodiments herein can be assigned to the other corresponding objects and vice versa. In other words, the systems can be improved with features described or claimed in the context of the corresponding method. In this case, the functional features of the methods are embodied by objective units of the systems.

According to a first embodiment, the invention relates to a computer-implemented method for generating modified medical images.

According to a further embodiment of the invention the second medical image is identical with the modified first medical image.

According to a further embodiment of the invention, a computer-implemented method is for generating modified medical images, comprising:

receiving a first medical image, the first medical image displaying an abnormal structure within a patient;

applying a trained inpainting function to the first medical image, thereby generating a modified first medical image, wherein the trained inpainting function is trained to inpaint abnormal structures within a medical image;

determining an abnormality patch based on the first medical image and the modified first medical image, in particular based on a difference of the first medical image and the modified first medical image;

receiving a second medical image, the second medical image being of the same type as the first medical image; and including the abnormality patch into the second medical image, thereby generating a modified second medical image.

According to an embodiment, in an alternative formulation, an embodiment of the invention relates to a computer-implemented method for generating modified medical images, comprising:

receiving a first medical image, the first medical image displaying an abnormal structure within a patient, applying a trained inpainting function to the first medical image, thereby generating a modified first medical image, wherein the trained inpainting function is trained to inpaint abnormal structures within a medical image, determining an abnormality patch based on the first medical image and the modified first medical image, in particular based on a difference of the first medical image and the modified first medical image, including the abnormality patch into the first medical image, thereby generating a twice-modified first medical image.

According to a second embodiment the invention relates to a generating system for generating modified medical images, comprising:

an interface, configured for receiving a first medical image, the first medical image displaying an abnormal structure within a patient, furthermore configure for receiving a second medical image, the second medical image being of the same type as the first medical image, a calculation unit configured for applying a trained inpainting function to the first medical image, thereby generating a modified first medical image, wherein the trained inpainting function is trained to inpaint abnormal structures within a medical image, furthermore configured for determining an abnormality patch based on the first medical image and the modified first medical image, in particular based on a difference of the first medical image and the modified first medical image, furthermore configured for including the abnormality patch into the second medical image, thereby generating a modified second medical image.

According to a third embodiment of the invention relates to a computer program or computer program product comprising instructions which, when the program is executed by a generating system, cause the generating system to carry out the method for generating modified medical images according to an embodiment of the invention and its aspects. In particular, an embodiment of the invention relates to a computer program or computer program product comprising instructions which, when the program is executed by the generating system according to the second an embodiment of the invention, cause the generating system to carry out the method for generating modified medical images according to an embodiment of the invention and its aspects.

According to a fourth embodiment, the invention relates to a computer-readable medium comprising instructions which, when executed by a generating system, cause the generating system to carry out the method for generating modified medical images according to an embodiment of the invention and its aspects. In particular, an embodiment of the invention relates to a computer-readable medium comprising instructions which, when executed by the generating system according to the second embodiment of the invention, cause the generating system to carry out the method for generating modified medical images according to an embodiment of the invention and its aspects.

According to a fifth embodiment, the invention relates to a computer-implemented method for detecting abnormal structures, comprising the steps of receiving a third medical image, and applying a trained detection function provided by the method of an embodiment to detect the abnormal structure within the third medical image.

According to a sixth embodiment, the invention relates to a detection system for detecting an abnormal structure, comprising: an interface configured for receiving a third medical image, a memory unit configured for storing a trained detection function provided by the method of an embodiment, and a calculation unit configured to apply the trained detection function to detect the abnormal structure within the third medical image.

According to another embodiment, a computer-implemented method comprises:
receiving a first medical image, the first medical image displaying an abnormal structure within a patient;
applying a trained inpainting function to the first medical image, to generate a modified first medical image, the trained inpainting function being trained to inpaint abnormal structures within a medical image;
determining an abnormality patch based on the first medical image and the modified first medical image;
receiving a second medical image, the second medical image being of a same type as the first medical image; and
including the abnormality patch into the second medical image, to generate a modified second medical image.

According to another embodiment, a generating system for generating modified medical images, comprises:
an interface, configured to
receive a first medical image, the first medical image displaying an abnormal structure within a patient,
receive a second medical image, the second medical image being of a same type as the first medical image; and
a processor configured to
apply a trained inpainting function to the first medical image to generate a modified first medical image, the trained inpainting function being trained to inpaint abnormal structures within a medical image,
determine an abnormality patch based on the first medical image and the modified first medical image, and
include the abnormality patch into the second medical image to generate a modified second medical image.

According to another embodiment, a non-transitory computer program product stores a program including instructions which, when the program is executed by a generating system, cause the generating system to carry out the method of an embodiment.

According to another embodiment, a non-transitory computer-readable medium stores instructions which, when executed by a generating system, cause the generating system to carry out the method of an embodiment.

According to another embodiment, a computer-implemented method for detecting an abnormal structure, comprises:
receiving a third medical image; and
applying a trained detection function provided by the method of an embodiment, to detect the abnormal structure within the third medical image.

According to another embodiment, a detection system for detecting an abnormal structure, comprises:
an interface, configured to receive a third medical image;
a memory, configured to store a trained detection function provided by the method of an embodiment; and
a processor, configured to apply the trained detection function to detect the abnormal structure within the third medical image.

BRIEF DESCRIPTION OF THE DRAWINGS

The properties, features and advantages of this invention described above, as well as the manner they are achieved, become clearer and more understandable in the light of the following description and embodiments, which will be described in detail in the context of the drawings. This following description does not limit the invention on the contained embodiments. Same components or parts can be labeled with the same reference signs in different figures. In general, the figures are not for scale.

The numbering and/or order of method steps is intended to facilitate understanding and should not be construed, unless explicitly stated otherwise, or implicitly clear, to mean that the designated steps have to be performed according to the numbering of their reference signs and/or their order within the figures. In particular, several or even all of the method steps may be performed simultaneously, in an overlapping way or sequentially.

Figure 1:
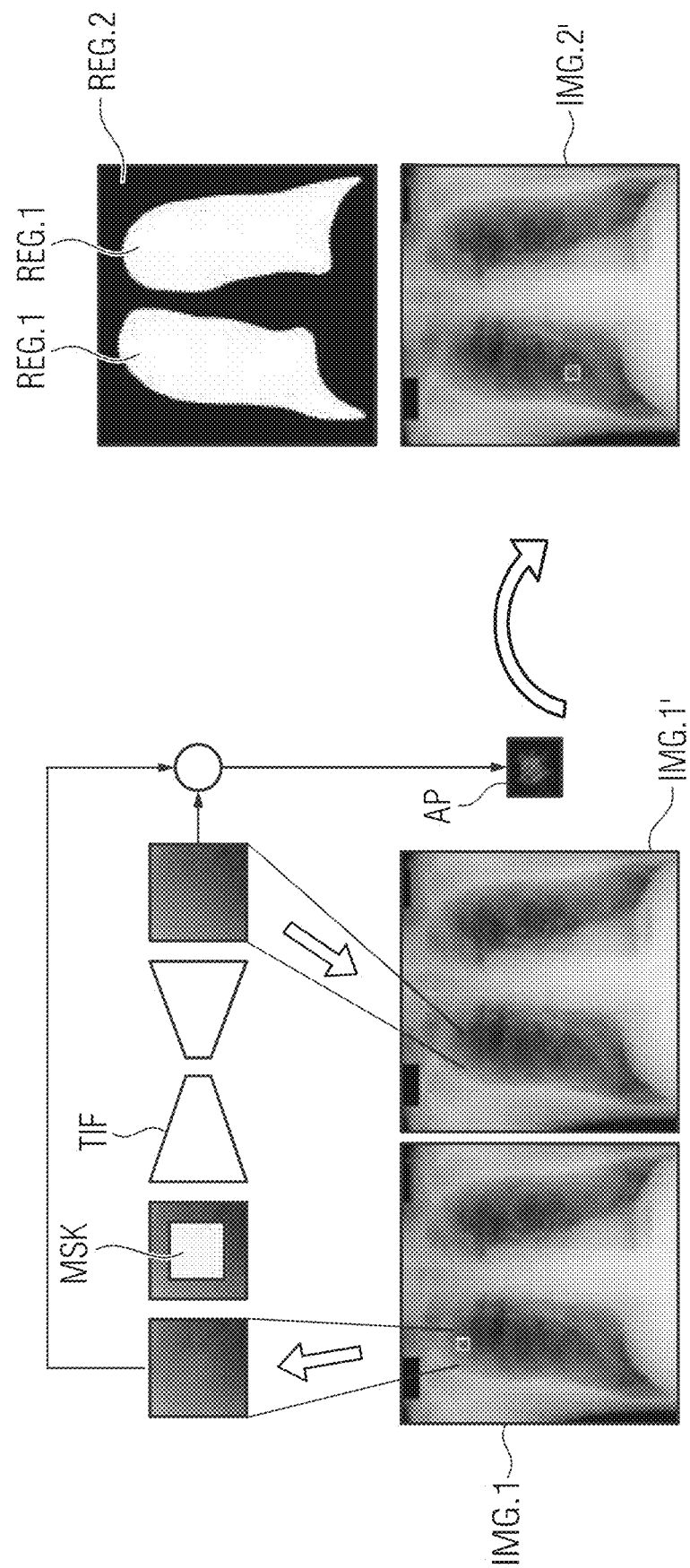
Figure 2:
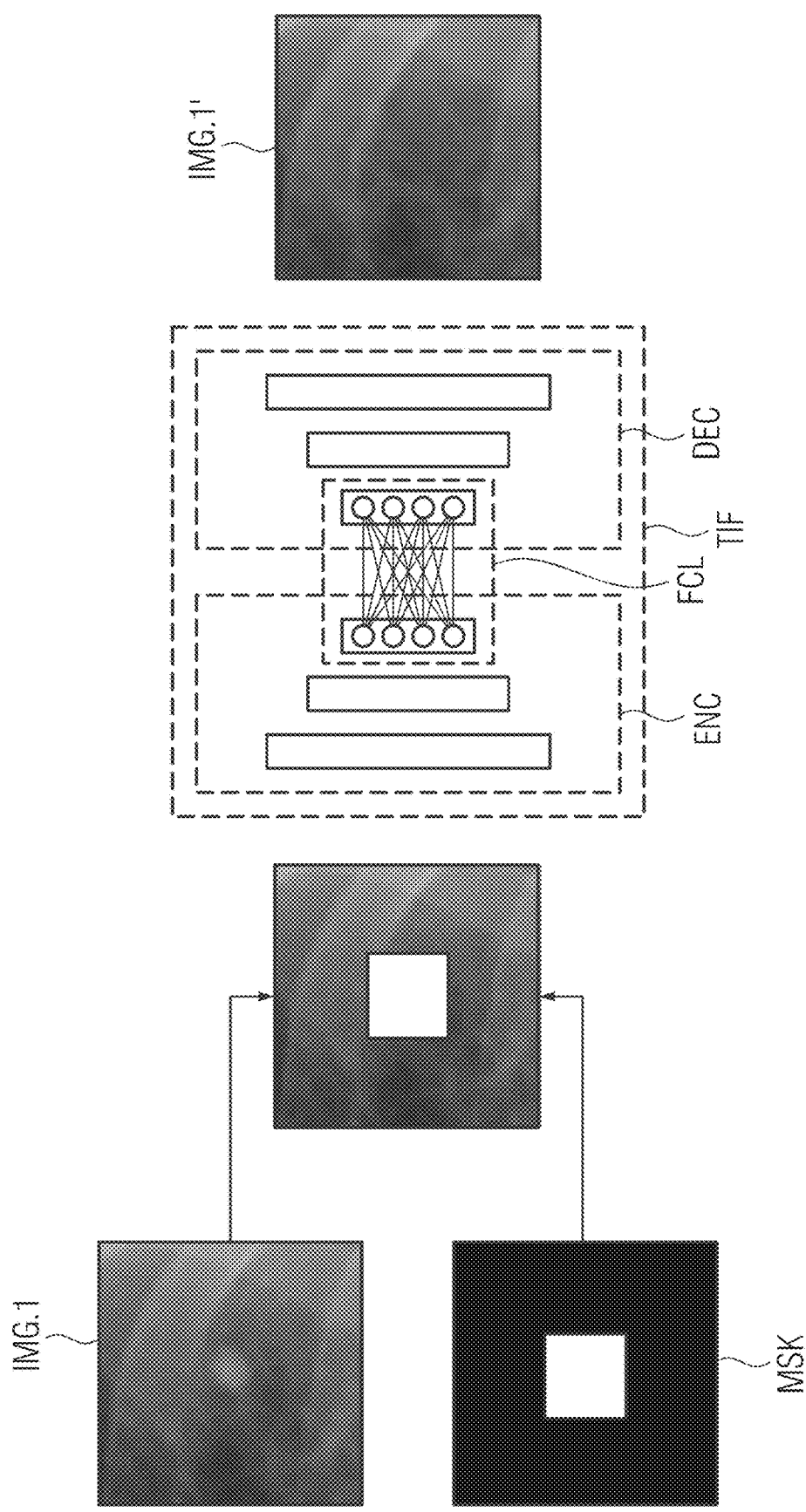
Figure 3:
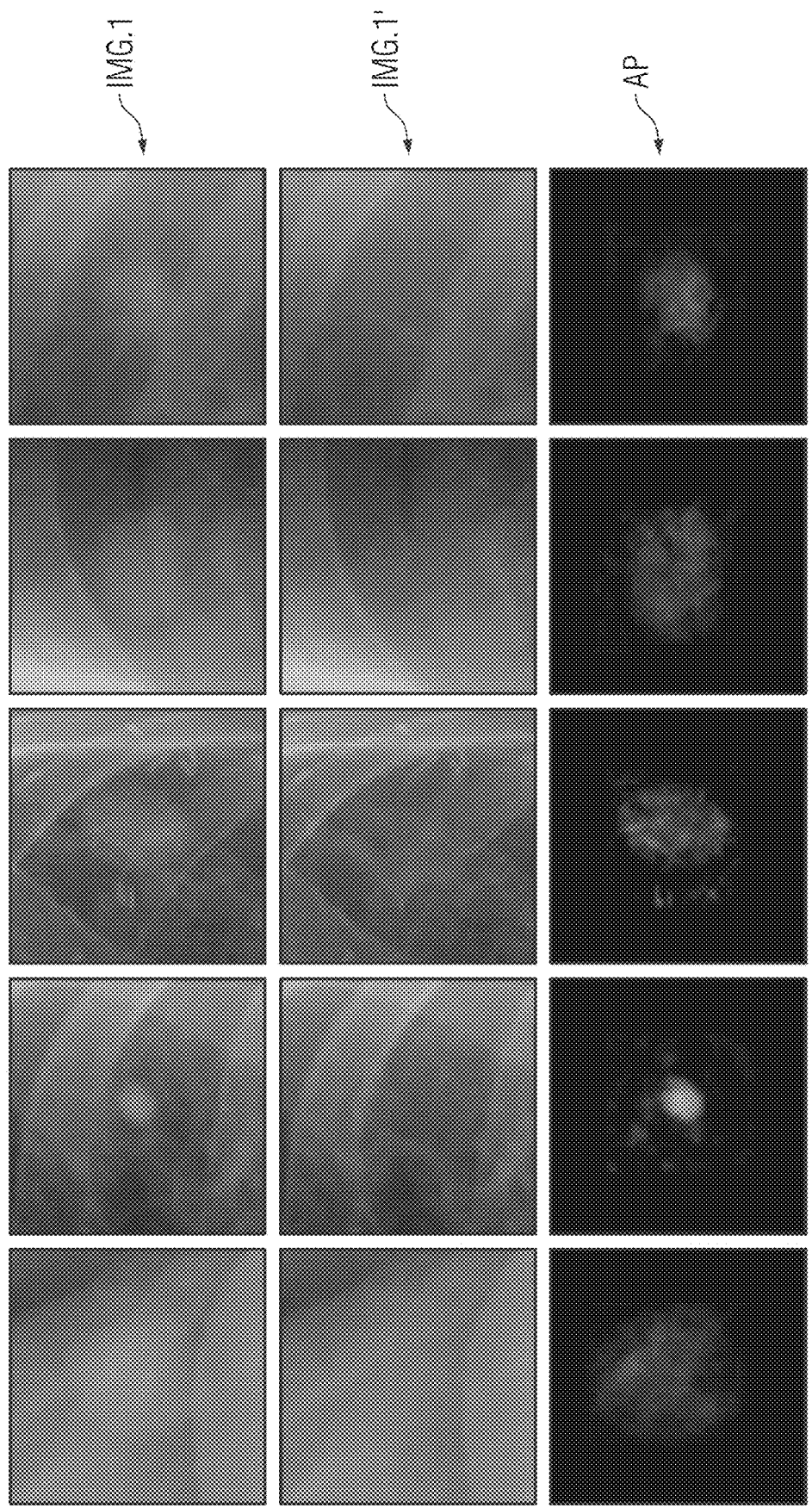
Figure 4:
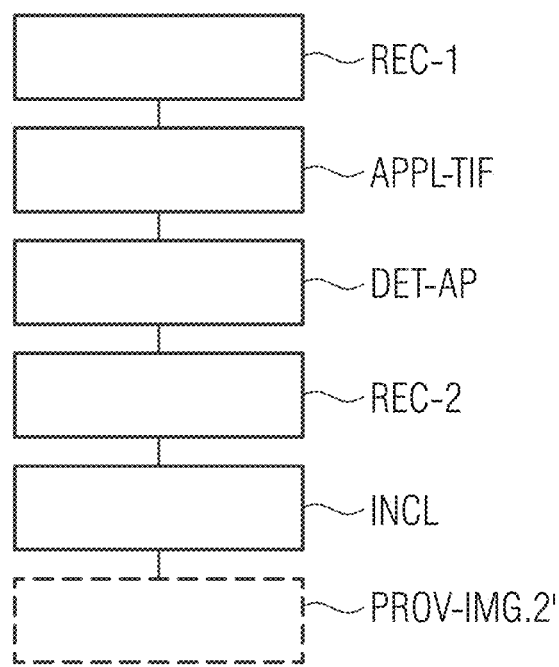
Figure 5:
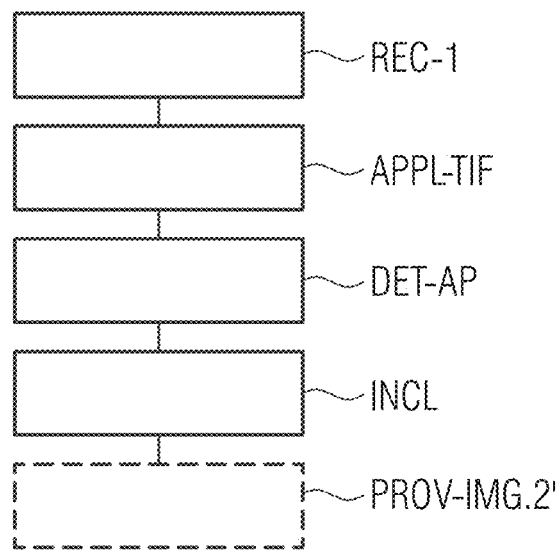
Figure 6:
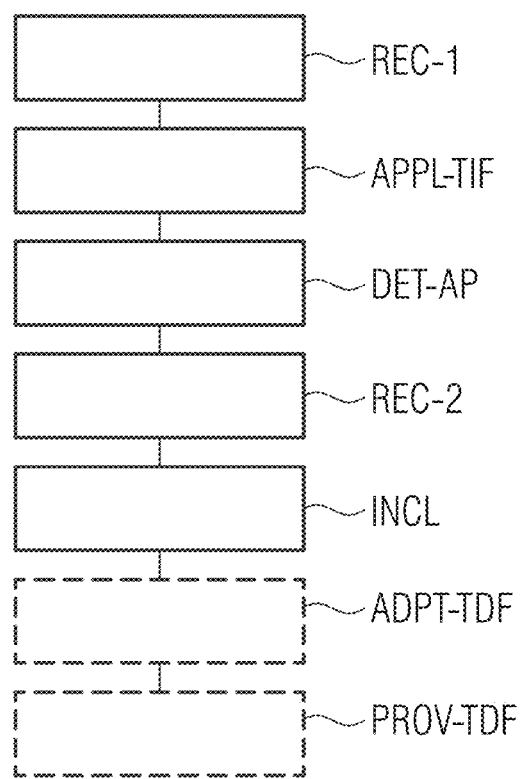
Figure 7:
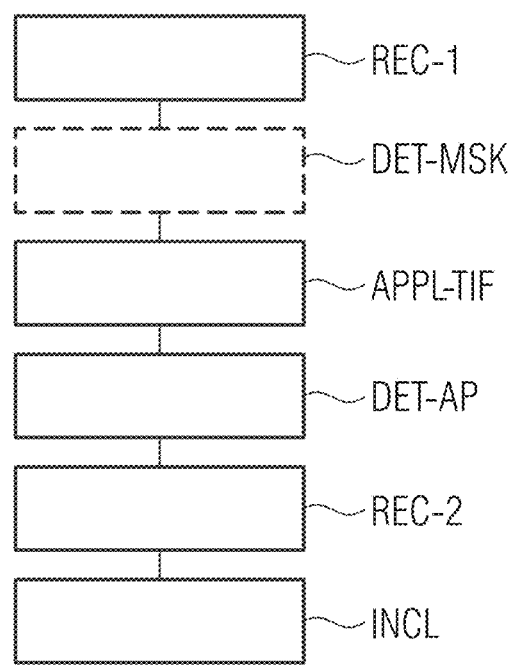
Figure 8:
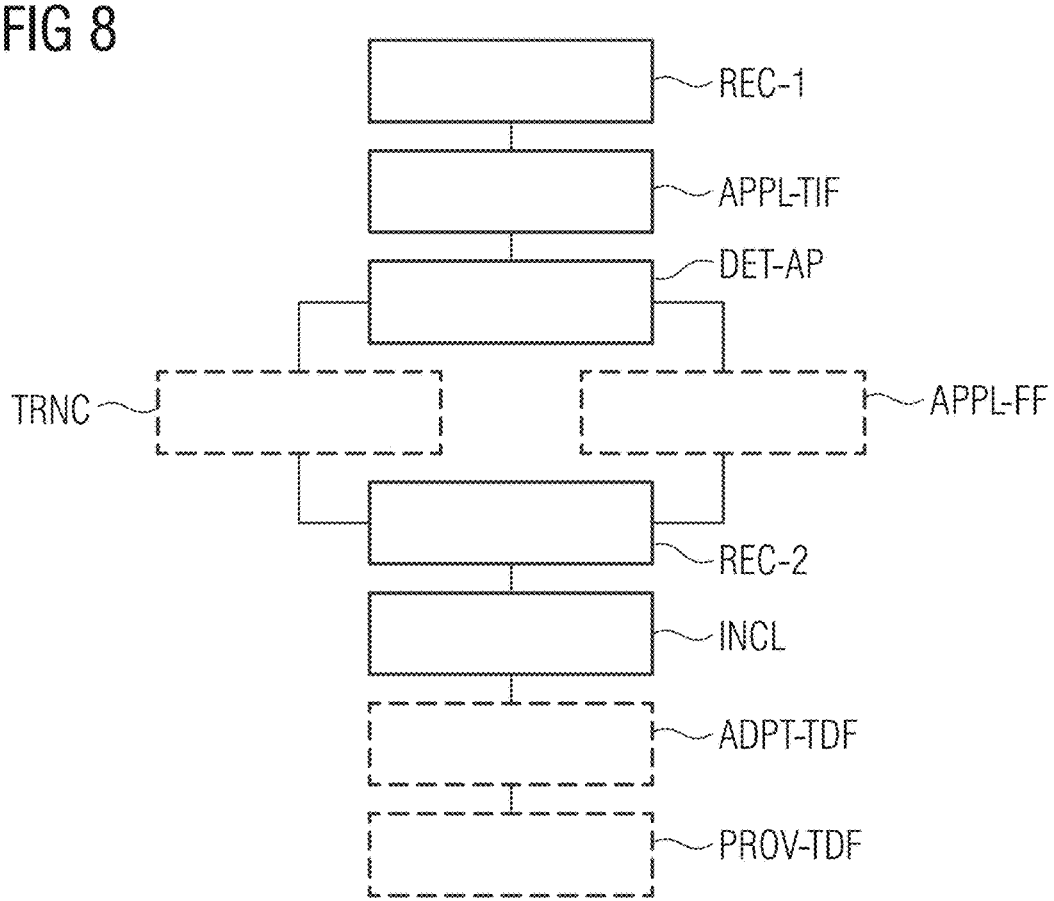
Figure 9:
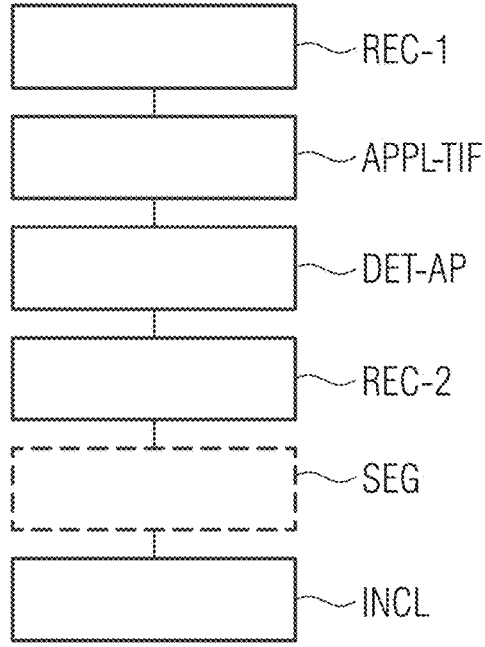
Figure 10:
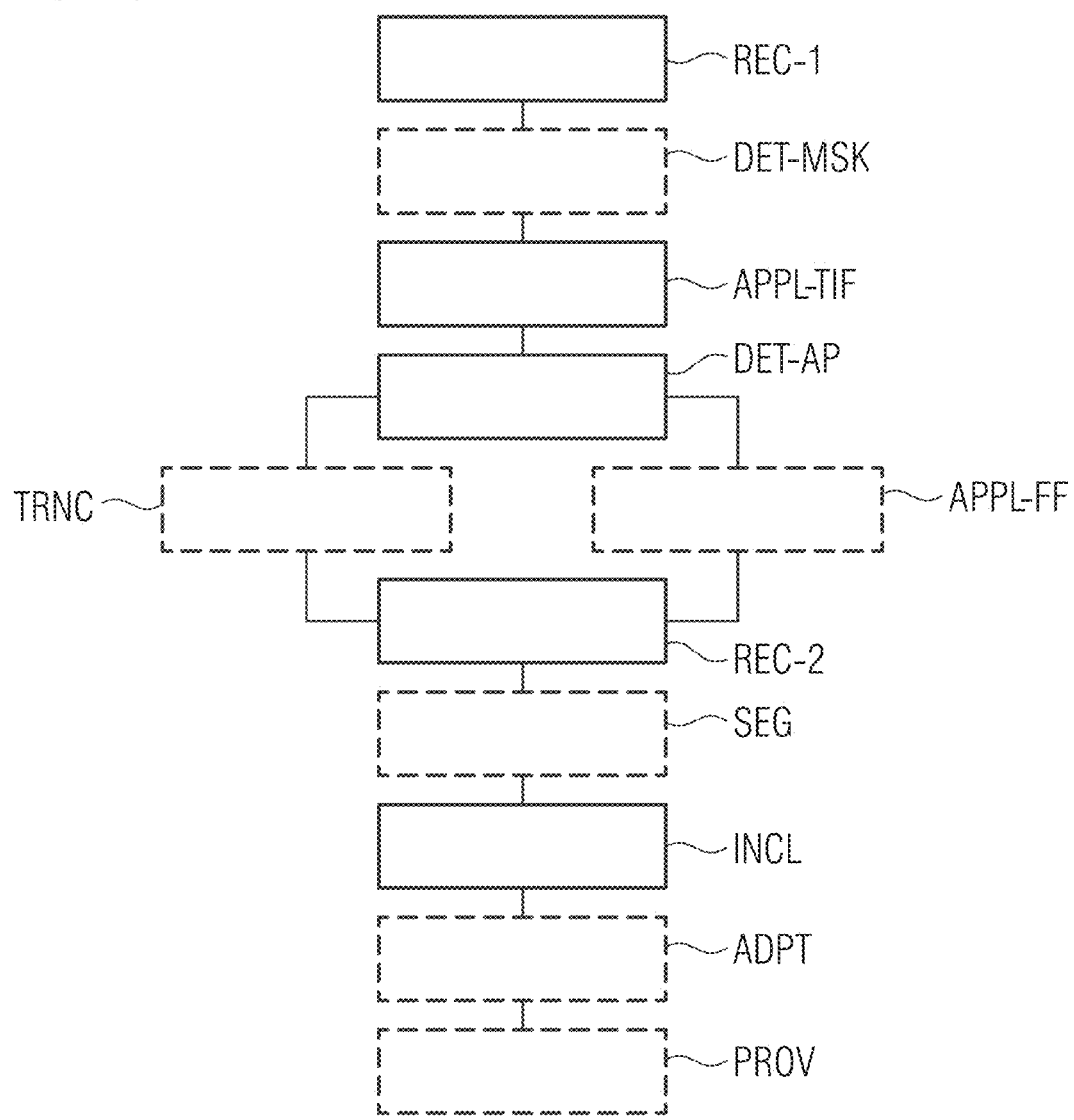
Figure 11:
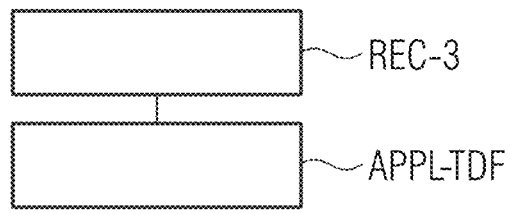
Figure 12:
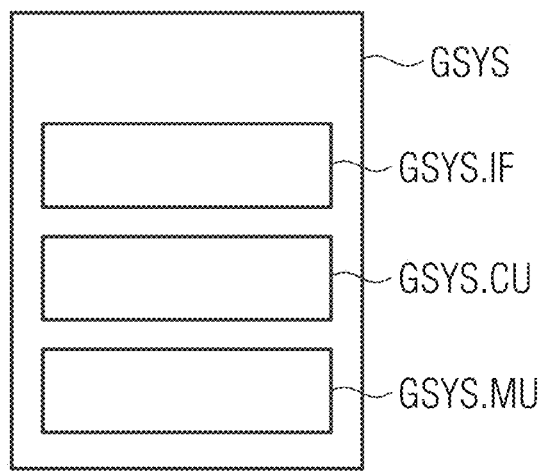
Figure 13:
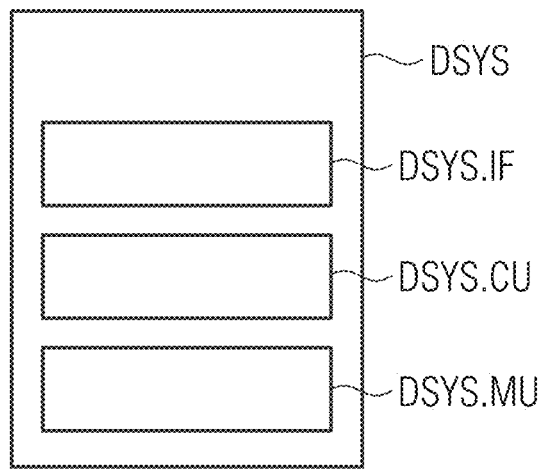

In the following:

FIG. 1 displays a sketch of the medical images and data structures used in the methods and systems according to the embodiments of the invention, FIG. 2 displays an embodiment of a trained inpainting function, FIG. 3 displays first medical images, modified first medical images and abnormality patches created by the trained inpainting function of FIG. 2, FIG. 4 displays a first embodiment of a computer-implemented method for generating modified medical images, FIG. 5 displays a second embodiment of a computer-implemented method for generating modified medical images, FIG. 6 displays a third embodiment of a computer-implemented method for generating modified medical images, FIG. 7 displays a fourth embodiment of a computer-implemented method for generating modified medical images, FIG. 8 displays a fifth embodiment of a computer-implemented method for generating modified medical images, FIG. 9 displays a sixth embodiment of a computer-implemented method for generating modified medical images, FIG. 10 displays a seventh embodiment of a computer-implemented method for generating modified medical images, FIG. 11 displays a flowchart of an embodiment of the method for detecting an abnormal structure, FIG. 12 displays a generating system for generating modified medical images, FIG. 13 displays a detection system for detecting an abnormal structure.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Bluray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to a first embodiment, the invention relates to a computer-implemented method for generating modified medical images. The method comprises receiving a first medical image, the first medical image displaying an abnormal structure within a patient, and applying a trained inpainting function to the first medical image, thereby generating a modified first medical image, wherein the trained inpainting function is trained to inpaint abnormal structures within a medical image.

The method furthermore comprises determining an abnormality patch based on the first medical image and the modified first medical image, in particular based on a difference of the first medical image and the modified first medical image.

The method furthermore comprises receiving a second medical image, the second medical image being of the same type as the first medical image. In particular, the second medical image is different from the first medical image. The method furthermore comprises including the abnormality patch into the second medical image, thereby generating a modified second medical image. In particular, including the abnormality patch can comprise a pixel-wise or voxel-wise sum of the second medical image and the abnormality patch, the sum defining the modified second medical image.

According to an embodiment, the method furthermore comprises providing the modified second medical image. Providing the modified second medical image can comprise displaying, storing and/or transmitting the modified second medical image.

In particular, the step of receiving the first medical image and receiving the second medical image, as well as the optional step of providing the modified second medical image can be executed by an interface, in particular, by an interface of a generating system for generating modified medical images. In particular, the steps of applying the trained inpainting function, of determining the abnormality patch and of including the abnormality patch into the second medical image can be executed by a computation unit, in particular, by a computation unit of the generating system for generating modified medical images.

In particular, the first and the second medical image can be two-dimensional medical images. In particular, the first and the second medical image can be three-dimensional images. In particular, the first and the second medical image can be four-dimensional images, where there are three spatial and one time-like dimensions.

In particular, the type of the medical image is related to the type of the medical imaging apparatus used for acquiring the medical image. For example, a first X-ray image and a second X-ray image are of the same type, even if they are recorded by different X-ray imaging apparatuses. In particular, the first medical image and the second medical image are of the same type if they correspond to the same body region (or region of interest) in the human body. For example, a first X-ray image of a human lung and a second X-ray image of a human knee are not of the same type, even if they relate to the same patient. However, a first X-ray image of a lung of a first patient and a second X-ray image of a lung of a second patient are of the same type.

In particular, the type of the medical image can be characterized by the modality used for creating the medical image and by the body region that is subject of the medical image. Optionally, the type of the medical image can also be characterized by parameters (of the imaging modality) used for creating the medical image (e.g., there could be the distinction between a "low dose image" and a "high dose image").

In particular, the first medical image and the second medical image can be medical images of the same patient. Alternatively, the second medical image can be a medical image of another patient.

A medical image can be identical with or encapsulated in one or more DICOM files. Whenever DICOM is mentioned herein, it shall be understood that this refers to the "Digital Imaging and Communications in Medicine" (DICOM) standard, for example according to the current DICOM PS3.1 2020c standard (or any later or earlier version of the standard).

In particular, an abnormal structure within a patient is an anatomical structure that differentiates the patients from other patients. In particular, an abnormal structure can be connected with a certain pathology of a patient.

The abnormal structure can be located within different organs of the patient (e.g. within the lung of a patient, or within the liver of a patient), the abnormal structure can also be located in between the organs of the patient. In particular, the abnormal structure could be a foreign body.

In particular, an abnormal structure can be a neoplasm (also denoted as "tumor"), in particular, a benign neoplasm, an in situ neoplasm, an malignant neoplasms and/or a neoplasms of uncertain/unknown behavior. In particular, an abnormal structure can be a nodule, in particular, a lung nodule.

In general, a trained function mimics cognitive functions that humans associate with other human minds. In particular, by training based on training data the trained function is able to adapt to new circumstances and to detect and extrapolate patterns.

In general, parameters of a trained function can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained functions can be adapted iteratively by several steps of training.

In particular, a trained function can comprise a neural network, a support vector machine, a decision tree and/or a Bayesian network, and/or the trained function can be based on k-means clustering, Qlearning, genetic algorithms and/or association rules. In particular, a neural network can be a deep neural network, a convolutional neural network or a convolutional deep neural network. Furthermore, a neural network can be an adversarial network, a deep adversarial network and/or a generative adversarial network.

In general, in the field of imaging the term inpainting denotes a process where missing parts of an image are filed in to create a completed image (without missing parts. In general, inpainting of images can be done manually or automatically, in particular, by image processing algorithms. In particular, automatic inpainting can utilize information within the images outside the missing parts to infer about the missing content of the missing parts of the image.

Inpainting algorithms can be based on structural and/or textural aspects of images. Furthermore, inpainting algorithms can be classical or learning-based inpainting algorithms. In particular, inpainting methods can also take into account external data not contained in the image (non-local algorithms).

In particular, inpainting can also be used for medical images, e.g. as in the document E. Sogancioglu et al., "Chest X-ray Inpainting with Deep Generative Models", arXiv: 1809.01471 (2018), the entore contents of which are hereby incorporated herein by reference.

The inventors recognized that by using the second modified medical images in the process of training a machine learning model (or, a trained detection function), the area under the curve (acronym AUC) increases compared to using non-augmented or standard augmented medical images as training images. This implies that the performance of machine learning models trained based on the provided second modified medical images increases compared to machine learning models trained on non-augmented or standard augmented medical images.

According to a further embodiment of the invention the second medical image is identical with the modified first medical image.

According to an embodiment, in an alternative formulation, an embodiment of the invention relates to a computer-implemented method for generating modified medical images, comprising:

receiving a first medical image, the first medical image displaying an abnormal structure within a patient, applying a trained inpainting function to the first medical image, thereby generating a modified first medical image, wherein the trained inpainting function is trained to inpaint abnormal structures within a medical image, determining an abnormality patch based on the first medical image and the modified first medical image, in particular based on a difference of the first medical image and the modified first medical image, including the abnormality patch into the first medical image, thereby generating a twice-modified first medical image.

The inventor recognized that by using the modified first medical image as second medical image fewer input data is necessary for creating the same amount of output training data. Furthermore, by using the modified first medical image as second medical image non-local characteristics (located outside of the abnormal structure, but causally linked with the abnormal structure) can be considered in the training of a machine learning model/trained detection function.

According to a further embodiment of the invention the first medical image and the second medical image are an X-ray image, a computed tomography image (acronym "CT image"), a magnetic resonance image (acronym "MR image"), a positron emission tomography image (acronym "PET image"), a single-photon emission computed tomography (acronym "SPECT image"), and/or an ultrasound image (acronym "US image"). Preferably, the first medical image and the second medical image are X-ray images of a chest of a patient.

According to a further embodiment of the invention the abnormal structure is a nodule, and wherein the abnormality patch is a nodule patch. According to a further embodiment of the invention the first medical image is a medical image of a lung of the patient, ant the abnormal structure is a lung nodule (also denoted as "pulmonary nodule"). In particular, also the second medical image is a medical image of a lung of a patient. A lung nodule can correspond to a benign tumor such as a granuloma or hamartoma, or to malignant cancer.

In particular, if the abnormal structure is a lung nodule, the first medical image and the second medical image are an X-ray image or an computed tomography image.

According to a further embodiment of the invention, the method furthermore comprises determining a mask corresponding to the abnormal structure within the first medical image, wherein applying the trained inpainting function to the first medical image and/or determining the abnormality patch are furthermore based on the mask. In particular, the abnormality patch and the mask have same dimensionality. In particular, the step of determining the mask can be executed by the calculation unit, in particular, by the calculation unit of the generating system for generating modified medical images.

In particular, applying the trained inpainting function being based on the mask can imply that the mask is used as an additional input to the trained inpainting function, or that the input if the trained inpainting function is based on a combination of the mask and the first medical image. In particular, applying the trained inpainting function based on the mask can imply that the first medical image and the modified first medical image differ only in the area defined in the mask. In other words, the effect of the trained inpainting function is limited by the mask located in the first medical image.

In particular, determining the abnormality patch based on the mask can imply that the mask is combined with the first medical image and/or the modified first medical image before determining the abnormality patch, or that the mask is combined with the combination (in particular, the difference) of the first medical image and the modified first medical image. In particular, the mask can be used to crop the first medical image and the modified first medical image, so that the abnormality patch is based on the difference of the cropped first medical image and the cropped modified first medical image.

The abnormality patch and the mask have the same dimensionality if the size of the abnormality patch with respect to every dimension (measured in number of pixels or voxels) is the same as the size of the mask with respect to the same dimension.

The inventors recognized that by using a mask in the described way noise outside the mask region can be suppressed, which leads to fewer artifacts in the modified first medical image and/or the modified second medical image.

According to a further embodiment of the invention the abnormality patch comprises pixels or voxels and the pixels or voxels comprise intensity values. According to this embodiment, the method furthermore comprises truncating pixels or voxels of the abnormality patch with negative intensity values. In particular, the step of truncating pixels or voxels of the abnormality patch can be executed by the calculation unit, in particular, by the calculation unit of the generating system for generating modified medical images.

In particular, each of the pixels or voxels of the abnormality patch comprises at least one intensity value. If the first medical image and the second medical image are X-ray images, the intensity values can correspond to an X-ray attenuation coefficient of the material imaged by the first and the second medical image. If the first medical image and the second medical image are computed tomography images, the intensity can be given in terms of Hounsfield units.

In particular, truncating a pixel or voxel can comprise replacing the intensity value of the respective pixel or voxel with a given constant other intensity value, in particular, replacing the intensity value of the respective pixel of voxel with 0.

The inventors recognized that abnormal structures, in particular nodules, correspond to pixels or voxels that are brighter (with an higher intensity value) than pixels without abnormal structures/nodules. This means that negative intensity values usually correspond to noise, and truncating those values leads to a better signal-to-noise ration of the generated images, and as a consequence, to better training performance.

According to a further embodiment of the invention the method comprises applying a filtering function to the abnormality patch. According to a potential further embodiment of the invention the filter function is a bilateral filtering function. In particular, the step of applying a filtering function can be executed by the calculation unit, in particular, by the calculation unit of the generating system for generating modified medical images.

In particular, a filter function is function that transforms an image into another image if the same dimensionality and the same size. In particular, a bilateral filtering function is a non-linear, edge-preserving, and noise-reducing smoothing filtering function. In particular, a bilateral filtering function replaces the intensity of each pixel or voxel with a weighted average of intensity values from nearby pixels or voxels. In particular, this weight can be based on a Gaussian distribution. In particular, the weights depend not only on Euclidean distance of pixels or voxels, but also on the radiometric differences (e.g., range differences, such as differences in the intensity values).

The inventors recognized that using filtering function, in particular, a bilateral filtering function smooths the abnormality patch and removes undesired background noise.

According to a further embodiment of the invention the method comprises segmenting the second medical image into a first region and a second region, wherein the first region is a region that can contain abnormal structures, and wherein the second region is a region that cannot contain abnormal structures. Furthermore, within the step of including the abnormality patch is included into the first region of the second medical image. In particular, the step of segmenting the second medical image can be executed by the calculation unit, in particular, by the calculation unit of the generating system for generating modified medical images.

In particular, segmenting the second medical image can be based on thresholding, region growing and/or edge detection. Alternatively, segmenting the second medical image can be based on a machine learning segmentation algorithm. Segmenting the second medical image can also be based on user input (e.g. based on a semi-automatic segmentation). Alternatively, other known segmentation methods can be used for segmenting the second medical image.

In particular, if the abnormal structure is a lung nodule, and if the second medical image is a medical image of the chest of a patient, the first region can correspond to the lung and the second region can correspond to the areas outside of the lung.

The inventors recognized that by determining the segmentation and by including the abnormality patch only into the first region more realistic modified second medical images can be generated, implying a better performance of machine learning models trained on those images.

According to a further embodiment of the invention within the step of including a transformation is applied to the abnormality patch, in particular, wherein the transformation is a rotation and/or a mirroring of the abnormality patch. In other words, within the step if including a transformed abnormality patch is included into the second medical image.

The inventors recognized that by using transformed abnormality patches a higher variability of modified second medical images can be achieved. A higher variability of training data for a machine learning model/trained detection function can help to prevent overfitting of the machine learning model/trained detection function.

Furthermore, rotations and/or mirroring do not qualitatively modify the abnormality patches and correspond to modifications of abnormalities that are anatomically possible, without having an impact on a diagnosis.

According to a further embodiment of the invention wherein the trained inpainting function comprises an artificial neural network, wherein the artificial neural network comprises a convolutional layer. Another term for an artificial neural network comprising a convolutional layer is "convolutional neural network".

The inventors recognized that convolutional neural networks are very suitable for image processing tasks. In particular, convolutional neural networks are very suitable for inpainting, and can lead to very exact results.

According to a further embodiment of the invention the artificial neural network is a context encoder network. In particular, a context encoder network can comprise at least one convolutional layer, however, this it is not necessary that a context encoder network comprises a convolutional layer.

In particular, a context encoder network comprises an encoder network and a decoder network. In particular, the encoder network takes as input the first medical image and optionally the mask (in particular, intensity values of pixels or voxels of the first medical image, in particular, intensity values of pixels or voxels of the first medical image outside of the mask) and maps it to a set of features. In particular, a feature can correspond to a number or a value of an output node of the encoder network. In particular, the number of features is less than the number of pixels or voxels used as input for the encoder). In particular, the decoder network takes as input a set features (in particular, each feature corresponding to a real number, and in particular, the number of features equivalent to the number of features created by the encoder network), and maps those features to at least a part of the modified first medical image. In particular, the features are mapped to the part of the first medical image corresponding to the mask. In particular, the last layer of the encoder network and the first layer of the decoder network can be connected by a channel-wise fully connected layer.

The inventors recognized that context encoders can produce very realistic inpaints. This implies that the abnormal structure can be extracted with only few noise corresponding to structures in the first medical image near the abnormal structure, but not causally linked to the abnormal structure. It follows that the content of the abnormality patch is in fact relating only or mainly to the abnormal structure, and not to those further structures.

According to a further embodiment of the invention, at least one parameter of the context encoder network is based on a spatially discounted reconstruction loss function. In the context of this invention, it is not necessary that the artificial trained inpainting function is a context encoder network for a parameter of the trained inpainting function being based on a spatially discounted reconstruction loss function. So, according to a further possible embodiment of the invention, at least one parameter of the trained inpainting function is based on a spatially discounted reconstruction loss function.

In particular, a spatially discounted reconstruction loss function is based on a weighting of the contribution of pixel or voxel intensities (in particular, for pixels or voxels predicted within the mask) to a loss function based on their spatial distance to a pixel or voxel with known intensity (in particular, pixels or voxels outside of the mask). In particular, the weighting can be an exponential function of the spatial distance.

The inventors recognized that missing pixels or voxels at the border of the inpainting region have less ambiguity, hence, those pixels and voxels should be weighted stronger during training in order to decrease border artifacts.

According to a further embodiment of the invention the method comprises adapting at least one parameter of a trained detection function based on the modified second medical image, and providing the trained detection function. Providing the trained detection function can comprise saving, transmitting and/or storing the trained detection function.

In particular, a trained detection function is a trained function taking as input a two-dimensional or three-dimensional medical image and that is configured by training to detect abnormal structures in the input medical images. In particular, the output of the trained detection function can correspond to the location and/or the severity of the abnormal structure. In particular, the location of the abnormal structure can be given by a single pixel of voxel (e.g., corresponding to the center of the abnormal structure), by a probability distribution assigning a probability value to several or all pixels or voxels (the probability value corresponding to the probability that a certain pixel or voxel corresponds to an abnormal structure within the patient), and/or by a bounding box circumventing the abnormal structure.

In particular, the trained detecting function is an artificial neural network comprising a convolutional layer and/or a pooling layer. In other words, the trained detection function is a convolutional neural network. Convolutional neural networks are very suitable for detecting structures in medical images.

The inventors recognized that using the modified second medical image in the training of a trained detection function creates a trained detection function with lower overfitting.

According to a further embodiment of the invention, training the trained detection function is based on a comparison of the location of abnormality patch in the modified second medical image and/or the severity of the abnormal structure corresponding to the abnormality patch with the output of the trained detection function. In particular, the severity of the abnormal structure can correspond to the grade of malignancy and/or benignancy of an abnormal structure being a tumor.

In particular, training the trained detection function is based on a comparison of the location of abnormality patch in the modified second medical image with the output of the trained detection function.

In particular, training the trained detection function is based on a comparison of the severity of the abnormal structure corresponding to the abnormality patch with the output of the trained detection function.

In particular, training the trained detection function is based on a comparison of the location of abnormality patch in the modified second medical image and the severity of the abnormal structure corresponding to the abnormality patch with the output of the trained detection function.

The inventors recognized that by inserting the abnormality patch into the second medical image the location of the abnormal structure within the modified second medical image can be determined very exactly, so that a very effective training of the trained detection function is possible. Furthermore, the severity of the abnormal structure can be determined based only on the abnormality patch, so that a plurality of training data can be generated and used in training based only on one first medical image.

According to a second embodiment the invention relates to a generating system for generating modified medical images, comprising:
- an interface, configured for receiving a first medical image, the first medical image displaying an abnormal structure within a patient,
- furthermore configure for receiving a second medical image, the second medical image being of the same type as the first medical image,
- a calculation unit configured for applying a trained inpainting function to the first medical image, thereby generating a modified first medical image, wherein the trained inpainting function is trained to inpaint abnormal structures within a medical image,
- furthermore configured for determining an abnormality patch based on the first medical image and the modified first medical image, in particular based on a difference of the first medical image and the modified first medical image, furthermore configured for including the abnormality patch into the second medical image, thereby generating a modified second medical image.

In particular, the generating system is configured to execute the previously described method for generating modified medical images and its embodiments. The generating system is configured to execute the previously described method for generating modified medical images and its embodiments by its interface and its calculation unit being configured to execute the respective method steps.

The generating system can be realized as a data processing system or as a part of a data processing system. Such a data processing system can, for example, comprise a cloud-computing system, a computer network, a computer, a tablet computer, a smartphone, a microprocessor or the like. The generating system can comprise hardware and/or software. The hardware can be, for example, a processor system, a memory system and combinations thereof. The hardware can be configurable by the software and/or be operable by the software.

Whenever modules like interfaces, computation units or memory units are mentioned herein, it shall be understood that this may refer to modules realized as hardware and/or as software. The modules are mentioned and described as a way of facilitating understanding, and it will be clear that all functions of all modules may be realized by one and the same body of computer program instructions (or: computer code). Moreover, the functions of any or all modules may overlap, and some modules may be integrated into other modules, without departing from the present disclosure. Furthermore, every module could also be a logical combination of several (identical or different) physical sub-modules that could also be distributed to various spatial locations.

According to a third embodiment of the invention relates to a computer program or computer program product comprising instructions which, when the program is executed by a generating system, cause the generating system to carry out the method for generating modified medical images according to the invention and its embodiments. In particular, an embodiment of the invention relates to a computer program or computer program product comprising instructions which, when the program is executed by the generating system according to the second an embodiment of the invention, cause the generating system to carry out the method for generating modified medical images according to an embodiment of the invention and its aspects.

According to a fourth embodiment, the invention relates to a computer-readable medium comprising instructions which, when executed by a generating system, cause the generating system to carry out the method for generating modified medical images according to an embodiment of the invention and its aspects. In particular, an embodiment of the invention relates to a computer-readable medium comprising instructions which, when executed by the generating system according to the second embodiment of the invention, cause the generating system to carry out the method for generating modified medical images according to an embodiment of the invention and its aspects.

The realization of an embodiment of the invention by a computer program product and/or a computer-readable medium has the advantage that already existing generating systems can be easily adopted by software updates in order to work as proposed by an embodiment of the invention.

The computer program product can be, for example, a computer program or comprise another element apart from the computer program. This other element can be hardware, for example a memory device, on which the computer program is stored, a hardware key for using the computer program and the like, and/or software, for example a documentation or a software key for using the computer program.

According to a fifth embodiment, the invention relates to a computer-implemented method for detecting abnormal structures, comprising the steps of receiving a third medical image, and applying a trained detection function provided by the method of an embodiment to detect the abnormal structure within the third medical image.

In particular, the third medical image is of the same type as the first medical image or the second medical image.

According to a sixth embodiment, the invention relates to a detection system for detecting an abnormal structure, comprising: an interface configured for receiving a third medical image, a memory unit configured for storing a trained detection function provided by the method of an embodiment, and a calculation unit configured to apply the trained detection function to detect the abnormal structure within the third medical image.

In particular, the detection system is configured to execute the previously described method for detecting abnormal structures and its embodiments. The detection system is configured to execute the previously described method for detecting abnormal structures and its embodiments by its interface and its calculation unit being configured to execute the respective method steps.

The detection system can be realized as a data processing system or as a part of a data processing system. Such a data processing system can, for example, comprise a cloud-computing system, a computer network, a computer, a tablet computer, a smartphone, a microprocessor or the like. The detection system can comprise hardware and/or software. The hardware can be, for example, a processor system, a memory system and combinations thereof. The hardware can be configurable by the software and/or be operable by the software.

The inventors recognized that based on the described method and detection system for detecting an abnormal structure the advantages described with respect to the other embodiments of the invention can be realized in the actual detection process of abnormal structures within medical images. In particular, due to a larger area under the curve compared with baseline methods the detection of abnormal structures is more exact and less error prone.

According to a potential seventh embodiment the invention relates to a computer program or computer program product comprising instructions which, when the program is executed by a detecting system, cause the detecting system to carry out the method for detecting an abnormal structure according to an embodiment of the invention and its aspects. In particular, the invention relates to a computer program or computer program product comprising instructions which, when the program is executed by the detecting system according to the sixth embodiment of the invention, cause the detecting system to carry out the method for detecting an abnormal structure according to an embodiment of the invention and its aspects.

According to a potential eighth embodiment, the invention relates to a computer-readable medium comprising instructions which, when executed by a detecting system, cause the detecting system to carry out the method for detecting an abnormal structure according to an embodiment of the invention and its aspects. In particular, an embodiment of the invention relates to a computer-readable medium comprising instructions which, when executed by the detecting system according to the sixth embodiment of the invention, cause the detecting system to carry out the method for detecting an abnormal structure according to the invention and its aspects.

FIG. 1

FIG. 1 displays a sketch of the medical images and data structures used in the methods and systems according to the embodiments of the invention.

Within the embodiment of FIG. 1, the first medical image IMG.1 is an X-ray image of a chest of a patient. Alternatively, first medical images IMG.1 based on other medical imaging modalities (e.g., computed tomography or magnetic resonance imaging) and/or of other parts of the body of a patient can be used. Furthermore, also the modified first medical image IMG.1' is an X-ray image of the chest of the patient. Note that the modified first medical image IMG.1' is not the direct result or output of a medical imaging examination (in this embodiment, in particular a medical imaging examination by a X-ray apparatus), but a synthetic medical image based on the first medical image IMG.1. In particular, the modified first medical image IMG.1' does not correspond to the actual anatomy of a patient.

Within this embodiment, the first medical image IMG.1 contains an abnormal structure being a lung nodule. So the first medical image IMG.1 can also be denoted as "nodule image" or "abnormality image". The modified first medical image IMG.1' does not depict an abnormal structure due to the modifications in its generation based on the first medical image IMG.1'. So the modified first medical image IMG.1' can also be denoted as "non-nodule image" or "non-abnormality image". For the chest X-ray images displays in FIG. 1, applying a standard classifier on the first medical image IMG.1 for nodule detection might result in a prediction (or probability for the presence of a lung nodule) of 92%, whereas applying the same standard classifier on the modified first medical image IMG.1' might result in a prediction of 11%.

For modifying the first medical image IMG.1 within this embodiment the first medical image IMG.1 is cropped to a smaller size. This is advantageous in the situation where the trained inpainting function TIF is configured to use input data having size smaller than the first medical image IMG.1. In this case, also the output of the trained inpainting function TIF corresponds to a cropped version of the modified first medical image IMG.1'. For the method and systems according to the invention and its embodiments it is not important whether cropped or un-cropped medical images are denotes as first medical image IMG.1 and modified first medical image IMG.1', since the un-cropped version of a medical image can be transformed to the cropped version by cropping, and the cropped version of a medical image can be transformed to the uncropped version by including the cropped version into remaining image data (e.g., the uncropped version of modified first medical image IMG.1' can be created by inserting the output of the trained inpainting function TIF, which corresponds to the cropped version, into the uncropped version of the first medical image IMG.1). The skilled person can determine based on the context of the specification whether the cropped or the uncropped version of medical image need to be used.

Within the embodiment, a rectangular mask MSK is used in the context of the first medical image IMG.1, and the trained inpainting function TIF is applied onto a combination of the rectangular mask MSK and the first medical image IMG.1. In particular, the mask MSK and the first medical image IMG.1 are combined by setting the intensities of all pixels within the first medical image IMG.1 that are inside the mask to a predefined value (e.g., the minimal or maximal possible value), leaving all pixels outside the mask unchanged, and using the result as input for the trained inpainting function TIF.

In the embodiment displayed in FIG. 1, the abnormality patch AP corresponds to a difference of the first medical image IMG.1 and the modified first medical image IMG.1'. The difference is a pixel-wise difference of the respective intensities of the pixels. Furthermore, the abnormality patch AP within this embodiment is cropped, here to the size and the position of the mask MSK, wherein this cropping is optional.

Furthermore, FIG. 1 displays the modified second medical image IMG.2'. Within this embodiment, there is no dedicated second medical image IMG.2, since the second medical image IMG.2 is equivalent to the modified first medical image IMG.1'. Alternatively, a different second medical image IMG.2 can be used. In the following description, reference is made to the second medical image IMG.2, wherein this term could also be replaced with the term "modified first medical image IMG.1'" if the second medical image IMG.2 and the modified first medical image IMG.1' are identical.

The modified second medical image IMG.2' is created by including the abnormality patch AP into the second medical image IMG.2. The process of including the abnormality patch AP can also be denoted as "local feature augmentation", and the modified second medical image IMG.2 can be denoted as "augmented image".

For including the abnormality patch AP, within this embodiment a segmentation of the second medical image IMG.2 into a first region REG.1 and a second region REG.2 is used. Here, the first region REG.1 corresponds to the lung of the patient within the second medical image IMG.2, and the second region REG.2 corresponds to the parts outside of the lung of the patient within the second medical image IMG.2. In this embodiment, for generating the modified second medical image IMG.2', the abnormality patch AP is included only into the first region REG.1, but not into the second region.

FIG. 2

FIG. 2 displays an embodiment of a trained inpainting function TIF being a context encoder network.

The context encoder network takes as an input a combination of a first medical image IMG.1 and a mask MSK. Alternatively, the context encoder network can also operate directly on the first medical image IMG.1. In the latter case, the context encoder network needs also to be trained for locating abnormal structures within the first medical image IMG.1. Furthermore, the context encoder network generates as output a modified first medical image IMG.2, wherein the context encoder inpaints meaningful intensities into the mask MSK area if the first medical image IMG.2.

In the displayed embodiment the context encoder comprises an encoder network ENC, a decoder network DEC and a fully connected layer FCL. The encoder network ENC comprises at least one, advantageously several convolutional layers, and advantageously also pooling layers. The decoder network DEC comprises at least one, advantageously several deconvolutional layers, and advantageously also pooling layers. The fully connected layer FCL is designed such that every node of the output layer of the encoder network ENC is connected with every node of the input layer of the decoder network DEC by an edge with adjustable or trainable weight. In this embodiment, the number of nodes in the output layer of the encoder network ENC is equivalent to the number of nodes in the input layer of the decoder network DEC, alternatively, those two numbers can also differ.

In this embodiment, the size of the first medical image IMG.1 and the modified medical image IMG.1' is 64×64 pixels, the size of the mask MSK and the size of the abnormality patch AP is 32×32 pixels. Within the encoder network ENC five layers with layer index $L_{enc}=\{0, 1, 2, 3, 4\}$ are used, within the decoder network DEC four layers with layer index $L_{dec}=\{0, 1, 2, 3\}$ are used. The network capacity is chosen such that the channel size is $c_L=2^{(8+L)}$ for encoder network ENC and $c_L=2^{(12-L)}$ for the decoder network DEC.

The training of the context encoder is based on comparison of known images and the same images combined with masks. In particular, a loss function is minimized, e.g. by using the backpropagation algorithm, and the loss function can be based on the squared or absolute pixel-wise difference of the original image and the inpainted image. For the training of the context decoder, within this embodiment an additional spatially discounted reconstruction loss is used in the training loss function. Missing pixels at the border have less ambiguity, hence, those pixels are weighted stronger during training. In this embodiment, the weights for each pixel are chosen as $\gamma^r$, where r denotes the nearest distance to the mask MSK border, and wherein γ is a constant factor. Within this embodiment, γ can be chosen in the interval between 0.95 and 0.99, advantageously γ is equivalent to 0.97.

Based on the described context encoder, the (p-th pixel of the) abnormality patch AP can be calculated as $n_p = \Theta_s(\max\{x_i-[TIF(x)]_p, 0\})$, wherein $x_p$ denotes the p-th pixel of the combination of the mask MSK with the first medical image IMG.1, $x^M_p = TIF(x)_p$ is equivalent to the (p-th pixel of the) modified first medical image IMG.1', and parameter $\Theta_s$ represents a bilateral filter with an advantageous filter size of s=3. The max operation corresponds to a truncation, since pixels with nodules are brighter than pixels without nodules, all negative values are truncated to 0.

Herein and in the following the index p is used as a multi-index and can. If the respective images are two-dimensional, the multi-index p (and later on q) represents two indices, e.g. i and j, so that $x_p = x_{ij}$. If the respective images are three-dimensional, the multi-index p represents three endices, e.g. i, j and k, so that $x_p = x_{ijk}$.

FIG. 3

FIG. 3 displays first medical images IMG.1, modified first medical images IMG.1' and abnormality patches AP created by the trained inpainting function TIF of FIG. 2 for four different first medical images IMG.1.

The training of the trained inpainting function TIF can be performed based on patches extracted at random position from images without abnormal structures. By training the trained inpainting function TIF as described with respect to FIG. 2 based on 1 million patches (for training), 10,000 patches (for validation), and 800 patches (for testing), a PSNR (acronym for "peak signal-to-noise ratio") of 34.22±3.95 can be achieved.

Approaches in, e.g. E. Sogancioglu et al., "Chest X-ray Inpainting with Deep Generative Models", arXiv: 1809.01471 (2018), claim a PSNR of 26.31±4.48. Applying this information to the very same training data set yields a signal-to-noise ratio of 31.24±3.77, still below the results of our choice of the trained inpainting function TIF.

FIG. 4

FIG. 4 displays a first embodiment of a computer-implemented method for generating modified medical images according to the invention and its aspects.

The first step of the displayed embodiment is receiving REC-1 a first medical image IMG.1. Here, the first medical image IMG-1 displays an abnormal structure within a patient.

In this embodiment, the first medical image IMG.1 as a two-dimensional X-ray image of the chest of the patient. The abnormal structure is a lung nodule within the chest of the patient. Alternatively, other types of medical images and other abnormal structures can be used within the method according to the invention and its embodiments.

The second step of the displayed embodiment is applying APPL-TIF a trained inpainting function TIF to the first medical image IMG.1, thereby generating a modified first medical image IMG.1'. Here, the trained inpainting function TIF is trained to inpaint abnormal structures within a medical image.

Denoting with x the first medical image IMG.1 and with $x^M$ the modified first medical image IMG.1', these two objects relate in this embodiment by $x^M = TIF(x)$ (where x and $x^M$ can be interpreted as vectors of real numbers, each pixel or voxel corresponding to an entry of the vector, and the intensity pixel or voxel corresponding to the numerical value of the entry of the vector).

Within this embodiment, the trained inpainting function TIF is the context encoder described within FIG. 2. Alternatively, the trained inpainting function TIF could be any other function trained to inpaint abnormal structures within a medical image, for example based on segmantic image inpainting or on a contextual attenuation model.

A further step of the displayed embodiment is determining DET-AP an abnormality patch AP based on the first medical image IMG.1 and the modified first medical image IMG-1'. In this embodiment, the abnormality patch AP is based on a difference of the first medical image IMG.1 and the modified first medical image IMG.1'. In particular, the abnormality patch can be a cropped difference of the first medical image IMG.1 and the modified first medical image IMG.1'. For example, the intensity value $n_p$ of the p-th pixel or voxel of the abnormality patch AP can be calculated as $n_p = x_p - [TIF(x)]_p = x_p - x^M_p$, only defined for the pixels or voxels in the surrounding of the abnormal structure. For example, the center of the abnormal structure can be defined as the pixel or voxel where $n_p = x_p - x^M_p$ is maximal, or by other known methods for detecting abnormal structures (in this embodiment, other methods for detecting lung nodules).

A further step of the displayed first embodiment is receiving REC-2 a second medical image IMG.2, the second medical image IMG.2 being of the same type as the first medical image IMG.1. In this first embodiment, the second medical image IMG.2 is also a two-dimensional X-ray image of a chest of a patient. In particular, the patient being subject of the second medical image IMG.2 is a different patient than the patient being subject of the first medical image IMG.1, and the second medical image IMG.2 is different from the modified first medical image IMG.1'.

Advantageously, the size of the second medical image IMG.2 (measured in number of pixels or voxels with respect to every dimension) is the same as the size of the first medical image IMG.1

A further step of displayed first embodiment is including INCL the abnormality patch AP into the second medical image, thereby generating a modified second medical image IMG.2'.

Denoting with y the second medical image IMG.2 and with $y^M$ the modified second medical image IMG.2', including INCL the abnormality patch AP can be executed as a pixel-wise or voxel-wise sum of the abnormality patch AP and the second medical image IMG.2, resulting in $y^M_p = y_p + n_q$, wherein the pixel or voxel q corresponds to the pixel or voxel p up to a linear offset (the linear offset being caused by the fact that the abnormality patch AP has a smaller size than the second medical image IMG.2, the linear offset determining the location where to insert the abnormality patch AP), and wherein $n_q = 0$ for undefined pixels or voxels.

The last, optional step of the displayed embodiment is providing PROV-IMG.2' the modified second medical image IMG.2', wherein providing PROV-IMG.2' the modified second medical image IMG.2' can comprise storing, displaying and/or transmitting the modified second medical image IMG.2'.

FIG. 5

FIG. 5 displays a second embodiment of a computer-implemented method for generating modified medical images according to the invention and its aspects.

Within the second embodiment, the second medical image IMG.2 is equivalent to the modified first medical image IMG.1'. This means that the step of receiving REC-2 the second medical image IMG.2 is already implicitly executed by the steps before. All other steps and advantageous features of the first embodiment can be transferred to the second embodiment, wherein the second medical image IMG.2 has to be replaced with the modified first medical image IMG.1.

For the following embodiments, the first embodiment displayed in FIG. 4 is used as a basis. However, equivalently the other embodiments could also be based on the flowchart of the second embodiment displayed within this FIG. 5.

FIG. 6

FIG. 6 displays a third embodiment of a computer-implemented method for generating modified medical images according to the invention an its aspects.

The third embodiment comprises all steps and advantageous features of the first embodiment displayed in FIG. 4. Furthermore, the third embodiment comprises the steps of adapting ADPT-TDF at least one parameter of a trained detection function based on the modified second medical image IMG.2', and providing PROV-TDF the trained detection function.

In the third embodiment, the abnormal structure is a lung nodule, and the trained detection function is configured to detect lung nodules in two-dimensional X-ray images of the chest of a patient.

In this embodiment, the trained detection function takes as input a two-dimensional X-ray image of the chest of a patient, and outputs coordinates of a bounding box marking potential lung nodules. If according to the trained detection function there is no lung nodule present, no or invalid coordinates are given as output. The trained detection function can also output coordinates of several bounding boxes. Trained detection functions for detecting abnormal structures in chest X-ray medical images are e.g. known from the patent document U.S. Pat. No. 10,691,980 B1, the entire contents of which are hereby incorporated herein by reference.

The modified second medical image IMG.2' can be used for the training together with the location where the abnormality patch AP was included (or, equivalently, with the abnormality patch AP as bounding box) as ground truth for the algorithm. This implies that no additional effort is needed for annotating the second medical image IMG.2'. Training the trained detection function can be done by training algorithms known to the person skilled in the art, e.g. using the backpropagation algorithm.

FIG. 7

FIG. 7 displays a fourth embodiment of a computer-implemented method for generating modified medical images according to the invention an its aspects.

The fourth embodiment comprises all steps and advantageous features of the first embodiment displayed in FIG. 4. Furthermore, the fourth embodiment comprises a step of determining DET-MSK a mask MSK corresponding to the abnormal structure within the first medical image IMG.1. Furthermore, the steps of applying APPL-TIF the trained inpainting function TIF to the first medical image IMG.1 and/or the step of determining DET-AP the abnormality patch AP are furthermore based on the mask MSK.

Within this embodiment, the abnormality patch AP and the mask MSK have same dimensionality. Both are two-dimensional images, and the size with respect to each of the dimensions (measured in pixel) is identical.

In particular, the mask MSK can be determined using a trained function trained for determining bounding boxes for abnormal structures in medical images, wherein the MSK is based on the bounding box or even equivalent with the bounding box. In our embodiment, these bounding boxes mark potential lung nodules in X-ray images of chests of patients. Such a trained function can be determined based on chest X-ray images, where a physician manually determined bounding boxes of such nodules. The size and/or the location of such a manually determined bounding box can then be used as ground truth for such a trained function.

Alternatively, instead of a bounding box a trained function (or any other algorithm for detecting abnormal structures like lung nodules) can be used for determining the pixel corresponding to the center of the abnormal structure. The mask MSK can then have a fixed, pre-determined size, and can be determined as centered with respect to the pixel determined.

For example, if M denotes the mask MSK being represented by two-dimensional image having the same dimensionality and size as x being the first medical image IMG.1, and $(i_0, j_0)$ correspond to the index of the pixel representing the center of the first medical image IMG.1, a quadratic mask MSK having a size of 2L+1 pixels can be represented as $M_{ij}=1$ for $i_0-L \leq i \leq i_0+L$ and $j_0-L \leq j \leq j_0+L$, and $M_{ij}=0$ otherwise.

In this embodiment applying APPL-TIF the trained inpainting function TIF being based on the mask MSK implies that the mask MSK is used as an additional input to the trained inpainting function TIF, so that the abnormality patch AP can be calculated as $n_p=x_p-[TIF(x, M)]_p=x_p-x^M_p$. Afterwards, the size of the abnormality patch AP can be reduced to the size of the mask MSK by cropping pixels or voxels outside of the mask. Alternatively, applying APPL-TIF the trained inpainting function TIF being based on the mask MSK implies that the input if the trained inpainting function TIF is based on a combination of the mask MSK and the first medical image IMG.1. For example, if $m_p=[x \cdot M]_p:=x_p \cdot M_p$ corresponds to the pixel-wise multiplication of the first medical image IMG.1 and the mask, the abnormality patch AP can be calculated as $n_p=x_p-TIF(x \cdot M)_p=x_p-x^M_p$. Afterwards, the size of the abnormality patch AP can be reduced to the size of the mask MSK by cropping pixels or voxels outside of the mask. In both cases, the size of the input values of the trained inpainting function TIF can be reduced by cropping pixels or voxels, so that the images used as input value have a predetermined dimensionality and/or so that the area of the mask is centered with respect to the images used input of the trained inpainting function TIF.

FIG. 8

FIG. 8 displays a fifth embodiment of a computer-implemented method for generating modified medical images according to the invention an its aspects.

The fifth embodiment comprises all steps and advantageous features of the first embodiment displayed in FIG. 4. Furthermore, the fifth embodiment comprises the step of truncating TRNC pixels or voxels of the abnormality patch AP with negative intensity values, and or the step of applying APPL-FF a filtering function to the abnormality patch AP. Within this embodiment the filtering function is a bilateral filtering function.

Truncating TRNC pixels or voxels of the abnormality patch AP can be done by using a max-function in the calculation of the abnormality patch AP as follows:

$$n_p=x_p-\max([TIF(x,M)]_p,0)=x_p-\max(x^M_p,0)$$

This implies that the abnormality patch AP comprises only positive intensity values.

Applying APPL-FF a filtering function to the abnormality patch AP can be implemented by using the filtered abnormality patch AP within the calculation of the modified second medical image IMG.2' as already described before:

$$y^M_p=y_p+\Theta(n)_q$$

Here, $\Theta$ defines the filtering function. For example, a bilateral filtering function is given by $$[\Theta_s(n)]_p=W^{-1}(n,q)\Sigma_{q \in S(p)}G_d(d(p,q)) \cdot G_I(|n_p-n_q|) \cdot n_q$$

Here p and q are multi-indices, S(p) is a surrounding of the pixel p (e.g. a quadratic or cubic mask around the pixel given by the multi-index p, e.g. with 3 pixels edge length), W is a weighting factor (for normalization, $W(n,q)=\Sigma_{q \in S(p)} G_d(d(p, q)) \cdot G_I(|n_p-n_q|)$), $G_d$ and $G_I$ are filtering kernels (e.g. Gaussian kernels), and d(p,q) is a distance function representing a distance (e.g. Euclidean distance or Manhattan distance) between the multi indices p an q.

FIG. 9

FIG. 9 displays a sixth embodiment of a computer-implemented method for generating modified medical images according to the invention an its aspects.

The sixth embodiment comprises all steps and advantageous features of the first embodiment displayed in FIG. 4. Furthermore, the sixth embodiment comprises the step of segmenting SEG the second medical image IMG.2 into a first region REG.1 and a second region REG.2, wherein the first region REG.1 is a region that can contain abnormal structures, and wherein the second region REG.2 is a region that cannot contain abnormal structures. Furthermore, within the step of including INCL the abnormality patch AP is included into the first region REG.1 of the second medical image IMG.1.

In particular, within this embodiment the abnormality patch AP is included into the first region REG.1 so that the abnormality patch AP is completely included into the first region REG.1, implying that there is no overlap between the abnormality patch AP and the second region REG.2. Alternatively, the abnormality patch AP can also be included into the first region REG.1 so that only the center of the abnormality patch AP is necessarily within the first region REG.1, implying that other parts of the abnormality patch AP can intersect with the second region.

In particular, within this embodiment segmenting SEG the second medical image IMG.2 is executed by using a trained segmentation function comprising a U-Net segmentation network.

FIG. 10

FIG. 10 displays a seventh embodiment of a computer-implemented method for generating modified medical images according to the invention an its aspects. The seventh embodiment combines all previous steps of the other embodiments. The steps displayed in the seventh embodiment are not necessarily executed in the order displayed in FIG. 10, they can also be executed in a different order or (at least partially) in parallel. Steps displayed in dashed lines are optional steps.

TABLE A

| Area under the curve for classification system trained based on the invention | | | | | | |
|---|---|---|---|---|---|---|
| Training set size | 100% | 70% | 50% | 20% | 10% | 5% |
| Training images | 79011 | 55307 | 39505 | 15802 | 7901 | 3950 |
| Baseline | 0.792 ± 0.010 | 0.776 ± 0.012 | 0.763 ± 0.009 | 0.722 ± 0.019 | 0.667 ± 0.007 | 0.649 ± 0.009 |
| Standard augment. | 0.795 ± 0.004 | 0.775 ± 0.008 | 0.769 ± 0.010 | 0.728 ± 0.013 | 0.681 ± 0.005 | 0.655 ± 0.007 |
| Invention | 0.805 ± 0.004 | 0.790 ± 0.005 | 0.781 ± 0.004 | 0.746 ± 0.005 | 0.705 ± 0.017 | 0.669 ± 0.013 |

Table A displays experimental data for a classification system for lung nodules trained on chest X-ray image modified by the invention and its embodiments.

For the experiments, data from the ChestX-ray14 (X. Wang et al., "ChestX-ray14: Hospital-scale Chest X-ray Database and Benchmarks on Weakly-Supervised Classification and Localization of Common Thorax Diseases", 2017, the entire contents of which are hereby incorporated herein by reference) and the JSRT database (J. Shiraishi J. et al., "Development of a digital image database for chest radiographs with and without a lung nodule: Receiver operating characteristic analysis of radiologists' detection of pulmonary nodules", In: AJR. pp. 71-74, 2000, the entire contents of which are hereby incorporated herein by reference) was used. The combined database contains 112,367 images with 6,485 nodule images. Nodule bounding boxes for 233 images are provided in the datasets.

In order to ensure that nodules are reliably removed for augmentation purposes, the modified first medical images IMG.1' images were individually validated. If the classification prediction (searching for the presence of lung nodules) was lower than the threshold 0.5 (possible values between 0.0 and 0.1), the corresponding abnormality patch AP was considered for the augmentation process. In addition to the training images, hence, 178 nodule patches could be included. The model was trained in following way: For each image and epoch a nodule patch was inserted with probability k. Accordingly, the corresponding nodule label was changed.

To evaluate the benefit of using the image augmentation method according to the invention on varying size of the training set, a learning curve analysis was performed. The network was trained with t % images of the training set and evaluated the performance. The dataset was split patient-wise into 70%, 10%, and 20% for training, validation, and testing, respectively. It was ensured that the images from the extracted nodule patches were present in the training set. For all experiments, a nodule insertion rate of k=0.05 was used. Each experiment was conducted 3 times. The resulting mean and standard deviation of the 3 runs is shown in Table A. The baseline is defined as being without any augmentation techniques (Row 1). Experiments were conducted with state-of-the-art augmentation on the full image. Random horizontal flipping and random rotation of the abnormality patches AP with a degree range of [−15, 15] was used. No significant improvement can be seen compared to the baseline model (Row 2). The evaluation of the local feature augmentation method according to the invention can be seen in Row 3. For each column the same training set was applied. For all training set sizes it can be stated that the augmentation method according to the invention consistently achieves better performance, compared to the baseline and standard augmentation method.

FIG. 11

FIG. 11 displays a flowchart of an embodiment of the method for detecting an abnormal structure, comprising the step receiving REC-3 a third medical image, and applying APPL-TDF a trained detection function provided by the method of according to one of the described embodiments for generating modified medical images to detect the abnormal structure within the third medical image.

In this embodiment, the third medical image is also a two-dimensional chest X-ray image of a breast of a patient, and the trained detection function is trained to detect lung nodules within the third medical image.

FIG. 12 & FIG. 13

FIG. 12 displays a generating system GSYS for generating modified medical images, FIG. 13 displays a detection system DSYS for detecting an abnormal structure. The generating system GSYS comprises an interface GSYS.IF, a computation unit GSYS.CU, and a memory unit GSYS.MU. The detection system DSYS comprises an interface DSYS.IF, a computation unit DSYS.CU, and a memory unit DSYS.MU.

The generating system GSYS and/or the detection system DSYS can be a (personal) computer, a workstation, a virtual machine running on host hardware, a microcontroller, or an integrated circuit. In particular, the generating system GSYS and/or the detection system DSYS can be mobile devices, e.g. a smartphone or a tablet. As an alternative, the generating system GSYS and/or the detection system DSYS can be a real or a virtual group of computers (the technical term for a real group of computers is "cluster", the technical term for a virtual group of computers is "cloud").

The generating system GSYS and/or the detection system can be connected to a network. The network can be realized as a LAN (acronym for "local area network"), in particular a WiFi network, or any other local connection, e.g. via Bluetooth or USB (acronym for "universal serial bus"). The network can alternatively also be realized as a VPN (acronym for "virtual private network").

An interface GSYS.IF, DSYS.IF can be embodied as a hardware interface or as a software interface (e.g. PCIBus, USB or Firewire). In particular, the interface GSYS.IF, DSYS.IF can be a combination of several other interfaces, in particular, the interface GSYS.IF, DSYS.IF can comprise one or more interfaces as subcomponent. In general, a computation unit GSYS.CU can comprise hardware elements and software elements, for example a microprocessor, a CPU (acronym for "central processing unit"), a GPU (acronym for "graphical processing unit"), a field programmable gate array (an acronym is "FPGA") or an ASIC. (acronym for "application-specific integrated circuit"). The computation unit GSYS.CU, DSYS.CU can be configured for multithreading, i.e. the computation unit GSYS.CU can host different computation processes at the same time, executing the either in parallel or switching between active and passive computation processes. In particular, the computation unit GSYS.CU, DSYS.CU can be a combination of several other computation units, in particular, the computation unit GSYS.CU, DSYS.CU can comprise one or more computation units as subcomponents. A memory unit GSYS.MU, DSYS.MU can be e.g. non-permanent main memory (e.g. random access memory) or permanent mass storage (e.g. hard disk, USB stick, SD card, solid state disk).

Wherever not already described explicitly, individual embodiments, or their individual aspects and features, can be combined or exchanged with one another without limiting or widening the scope of the described invention, whenever such a combination or exchange is meaningful and in the sense of this invention. Advantages which are described with respect to one embodiment of the present invention are, wherever applicable, also advantageous of other embodiments of the present invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method, comprising:
   receiving a first medical image, the first medical image displaying an abnormal structure within a patient;
   applying a trained inpainting function to the first medical image, to generate a modified first medical image, the trained inpainting function being trained to inpaint abnormal structures within a medical image;
   determining an abnormality patch based on the first medical image and the modified first medical image;
   receiving a second medical image, the second medical image being of a same type as the first medical image; and
   generating a modified second medical image by including the abnormality patch in the second medical image.

2. The method of claim 1, wherein the second medical image is identical to the modified first medical image.

3. The method of claim 1, wherein the first medical image and the second medical image are at least one of:
   an X-ray image,
   a computed tomography image,
   a magnetic resonance image,
   a positron emission tomography image,
   a single-photon emission computed tomography, or
   an ultrasound image.

4. The method of claim 1, wherein the abnormal structure is a nodule, and wherein the abnormality patch is a nodule patch.

5. The method of claim 4, wherein the first medical image is medical image of a lung of the patient, and wherein the abnormal structure is a lung nodule.

6. The method of claim 1, further comprising:
   determining a mask corresponding to the abnormal structure within the first medical image,
   wherein at least one of the applying of the trained inpainting function to the first medical image or the determining of the abnormality patch is further based on the mask.

7. The method of claim 6, wherein the abnormality patch and the mask have a same dimensionality.

8. The method of claim 1, wherein
   the abnormality patch includes pixels or voxels, the pixels or voxels including intensity values, and
   the method further includes truncating pixels or voxels of the abnormality patch with negative intensity values.

9. The method of claim 1, further comprising:
   applying a filtering function to the abnormality patch.

10. The method of claim 9, wherein the filter function is a bilateral filtering function.

11. The method of claim 1, further comprising:
    segmenting the second medical image into a first region and a second region, the first region being a region configured to contain abnormal structures, and the second region being a region configured to not contain abnormal structures, and
    wherein the generating the modified second medical image includes including the abnormality patch in the first region of the second medical image.

12. The method of claim 1, wherein generating the modified second medical image includes applying a transformation to the abnormality patch.

13. The method of claim 12, wherein the transformation is at least one of a rotation or a mirroring of the abnormality patch.

14. The method of claim 1, wherein the trained inpainting function includes an artificial neural network, and wherein the artificial neural network includes a convolutional layer.

15. The method of claim 14, wherein the artificial neural network is a context encoder network.

16. The method of claim 15, wherein at least one parameter of the context encoder network is based on a spatially discounted reconstruction loss function.

17. The method of claim 1, further comprising:
    adapting at least one parameter of a trained detection function based on the modified second medical image, and
    providing the trained detection function.

18. The method of claim 17, wherein training the trained detection function is based on a comparison of at least one of a location of the abnormality patch in the modified second medical image or a severity of the abnormal structure corresponding to the abnormality patch.

19. A computer-implemented method for detecting an abnormal structure, the computer-implemented method comprising:
    receiving a third medical image; and
    applying a trained detection function provided by the method of claim 18, to detect the abnormal structure within the third medical image.

20. A computer-implemented method for detecting an abnormal structure, the computer-implemented method comprising:
    receiving a third medical image; and
    applying a trained detection function provided by the method of claim 17, to detect the abnormal structure within the third medical image.

21. A detection system for detecting an abnormal structure, the detection system comprising:
    an interface configured to receive a third medical image;
    a memory configured to store a trained detection function provided by the method of claim 17; and
    a processor configured to apply the trained detection function to detect the abnormal structure within the third medical image.

22. A non-transitory computer program product storing a program including instructions which, when the program is executed by a generating system, cause the generating system to carry out the method of claim 1.

23. A non-transitory computer-readable medium storing instructions which, when executed by a generating system, cause the generating system to carry out the method of claim 1.

24. The method of claim 1, wherein the determining of the abnormality patch is based on a difference between the first medical image and the modified first medical image.

25. A generating system for generating modified medical images, comprising:
    an interface configured to
      receive a first medical image, the first medical image displaying an abnormal structure within a patient, and
      receive a second medical image, the second medical image being of a same type as the first medical image; and a processor configured to
- apply a trained inpainting function to the first medical image to generate a modified first medical image, the trained inpainting function being trained to inpaint abnormal structures within a medical image,
- determine an abnormality patch based on the first medical image and the modified first medical image, and
- generate a modified second medical image by including the abnormality patch in the second medical image.

26. The generating system of claim 25, wherein the processor is configured to determine the abnormality patch based on a difference between the first medical image and the modified first medical image.

* * * * *